United States Patent [19]

Föry et al.

[11] 4,053,497

[45] Oct. 11, 1977

[54] AGENT FOR THE REGULATION OF PLANT GROWTH

[75] Inventors: Werner Föry, Basel; Hanspeter Fischer, Bottmingen; Dieter Lohmann, Pratteln; Gerd Greber, Binningen, all of Switzerland

[73] Assignee: Ciba-Geigy Corporation, Ardsley, N.Y.

[21] Appl. No.: 709,828

[22] Filed: July 29, 1976

Related U.S. Application Data

[63] Continuation of Ser. No. 341,447, March 15, 1973, abandoned.

[30] Foreign Application Priority Data

Mar. 29, 1972 Switzerland .......................... 4671/72
Mar. 29, 1972 Switzerland .......................... 4733/72

[51] Int. Cl.$^2$ ................................................. C07F 7/18
[52] U.S. Cl. .................................. 260/448.8 R; 71/70; 71/79
[58] Field of Search .................................. 260/448.8 R

[56] References Cited

U.S. PATENT DOCUMENTS 3,928,406  12/1975  Leeper et al. ................. 260/448.8 R Primary Examiner—Paul F. Shaver
Attorney, Agent, or Firm—Harry Falber

[57] ABSTRACT

The present invention relates to new compositions and methods for the regulation of plant growth, especially for fruit abscission, acceleration of ripening and latex discharge of rubber trees, and to new active substances of the class of β-halogenoethylsilanes.

6 Claims, No Drawings

AGENT FOR THE REGULATION OF PLANT GROWTH

This is a continuation of application Ser. No. 341,447 filed on Mar. 15, 1973, now abandoned.

The present invention relates to new compositions and methods for the regulation of plant growth by the use of new β-halogenoethyl-silanes as active substances, also to new β-halogenoethyl-silanes and to processes for the production of these silanes.

The β-halogenoethyl silanes contained as active substances in the new agents correspond to formula I

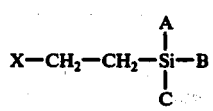

(I)

The symbols in this formula have the following meanings:

X represents chlorine or bromine,

A represents a radical —S—$R_1$,

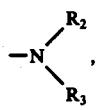

—O$R_4$, —CH=$CH_2$ or —$CH_2$—$CH_2$—X, and B and C each independently represent $CH_3$, —CH=$CH_2$ or —$CH_2$—$CH_2$—X.

The symbol $R_1$ represents an alkyl radical, an alkyl radical substituted by alkoxycarbonyl, phenyl, cycloalkyl or a heterocyclic radical, as well as alkenyl, alkynyl, cycloalkyl and cycloalkenyl; a phenyl radical optionally mono- or polysubstituted by alkyl, aloxy, alkylthio and/or halogen; and a benzyl radical optionally mono- or polysubstituted by alkyl, alkoxy, alkylthio and/or halogen.

The symbol $R_3$ represents alkyl which can be substituted by alkoxy, alkylthio, phenyl, cycloalkyl, or by a heterocyclic radical; also cycloalkyl, cycloalkenyl, alkenyl, alkynyl; phenyl optionally mono- or polysubstituted by alkyl, alkoxy, alkylthio and/or halogen; and benzyl optionally mono- or polysubstituted by alkyl, alkoxy, alkylthio and/or halogen.

The symbol $R_2$ represents hydrogen, or the same as $R_3$, whereby $R_2$ and $R_3$ together with the adjacent nitrogen atom can however also form a saturated or unsaturated ring system.

The symbol $R_4$ represents an alkyl radical; an alkyl radical substituted by halogen or by alkoxy, alkanoyloxy, aroyloxy, aryloxy, alkoxyalkoxy, alkenyloxy, phenoxy, cycloalkyl, alkylthio and/or alkoxycarbonyl or by a heterocyclic radical; alkenyl or halogenoalkenyl, alkynyl, cycloalkyl, cycloalkenyl; a phenyl radical optionally mono- or polysubstituted by cyano, nitro, alkyl, halogenoalkyl, alkoxy, alkylthio, alkanoyl and/or alkoxycarbonyl; and a benzyl radical optionally mono- or polysubstituted by alkyl, alkoxy and/or halogen.

The symbol $R_4$ can however also represent the group —CO—$R_5$ wherein $R_5$ stands for an alkyl, alkenyl or alkynyl radical, a halogenoalkyl or halogenoalkenyl radical, an alkyl or alkenyl radical substituted by phenyl, where phenyl can be substituted by alkyl, alkoxy and/or halogen; an alkoxyalkyl radical, an alkoxycarbonylalkyl radical, a benzoylalkyl radical, a cycloalkylalkyl radical or a phenyl radical which can optionally be substituted by halogen, lower alkyl or alkoxy, and, finally, for a 5- or 6-membered heterocyclic radical.

By alkyl radicals are meant straight-chain or branched radicals having 1 to 18 carbon atoms, such as, e.g. methyl, ethyl, n-propyl, isopropyl, n-butyl, sec-butyl, n-hexyl, n-octyl, n-dodecyl, n-octadecyl, and so forth. It is particularly the straight-chain and branched alkyl radicals having 1 to 8 carbon atoms which form the alkyl moiety of alkoxy, alkylthio or alkoxycarbonyl substituents of an alkyl radical or of a phenyl radical. In the case of halogenoalkyl radicals, these are alkyl radicals having 1 to 6 carbon atoms, which can be substituted by fluorine, chlorine and/or bromine, such as, e.g. trifluoromethyl, 2-chloroethyl, 6-chlorohexyl, etc.. Alkenyl radicals are straight-chain or branched radicals having 3 to 18 carbon atoms, e.g. propenyl, butenyl, octenyl, decenyl or heptadecenyl radicals.

These alkenyl radicals can be mono- or polysubstituted by halogen, such as fluorine, chlorine, bromine and/or iodine. Alkenyl radicals having 3 to 6 carbon atoms form the alkenyl moiety of alkenyloxy radicals. Alkynyl radicals preferably contain 3 to 8 carbon atoms in a straight chain, such as, e.g. 2-propynyl, 2-butynyl or 3-hexynyl. By cycloalkyl and cycloalkenyl radicals are meant mono- and polycyclic radicals having 3 to 12 carbon atoms, such as, e.g. cyclopropyl, cyclopentyl, cyclopentenyl, cyclohexyl, cyclohexenyl or bicycloheptyl, etc..

The β-halogenoethyl-silanes of formula I affect in a varying manner the growth of parts of plants above and below the soil, and have a low toxicity towards warmblooded animals. The active substances cause no morphological changes or damage which would result in the withering of the plant. The compounds are not mutagenic. Their action differs from that of a herbicidal active substance and of a fertiliser. The action corresponds more to the effects which can be observed on application of ethylene to various parts of plants. It is known that the plant itself produces, in various stages of development, ethylene to a varying degree, particularly before and during the ripening process of the fruits, and at the end of the vegetation period with the occurring abscission of fruit and leaves. Since the regulation of ripening and of fruit and leaf abscission by application of chemical substances is of the greatest commercial importance in the cultivation of fruit, citrus fruit, pineapples and cotton, efforts have been directed towards the discovery of compounds with which such effects might be obtained, without the treated plants suffering any kind of damage in the process. Thus, various classes of substances have meanwhile become known with which it has been possible to obtain some of the growth-regulating effects referred to; however, the extent of the range of action of these substances corresponds in no way to that of ethylene. Compounds which under certain conditions release ethylene are known. Such compounds have the disadvantage either in that they are relatively unstable under the influences of weather, because they are very susceptible to hydrolysis, or in that they are phytotoxic. In the South African Patent Specification No. 68/1036, β-halogenoethyl-phosphonic acid derivatives are described as active substances which regulate plant growth. These compounds decompose in and on the plant with the release of ethylene, and are therefore similar in action and range of action to ethylene. By virtue of their very low stability, phosphonic acid derivatives are not able, however, to satisfy the demands made on them. As they are stable only in an acid medium, more precisely in a pH-range below 5, the active-substance concentrates have to be stabilised by the addition of acids. This addition of acid however, limits the range of application of these active substances in view of the resulting phytotoxic effects. Furthermore, the storage of such sensitive concentrates of active substance presents difficulties.

Further compounds known as herbicidal active substances are halogenoalkyl-methyl-silanes [cp. U.S.-Patent Specifications Nos. 3,390,976 and 3,390,977, and J. K. Leasure et al., J. Med. Chem. 9, 949 (1966)]. $\beta$-Chloroethylmethyl-dimethoxysilane was produced by J. K. Leasure et al. (loc.cit), but has no herbicidal action. The U.S.-Patent Specification No. 3,183,076 describes $\alpha$-chloroethylmethyl-dialkoxysilanes, which can be used for the promotion of germination power, leaf abscission, etc..

The present invention relates to new agents containing as active substances $\beta$-halogenoethyl-silanes, which have a stimulating or retarding action on plant growth in the various stages of development of the plants. These agents can contain the usual carrier substances, distributing agents, and stabilisers protecting against the effects of light and of oxidation. The action of the new agents is to regulate vegetative plant growth and germination power, and to promote the formation of blossom, the development of fruit and the growth of abscission layers. In the case of monocotyledons, an increase in tillering and branching was observed with a simultaneous reduction of growth in height. There was moreover a strengthening of the support tissues of the stalks in the case of the treated plants. The formation of undesirable side shoots on various types of plants is very greatly reduced; for example, the vegetative growth of grape vines is inhibited. The new compounds also have a secretion-promoting action; for example, the latex discharge in the case of Hevea brasiliensis is promoted, an effect which is of great commercial importance. As tests have shown, the rooting of seedlings and cuttings, as well as the development of tubers in the case of potatoes, is promoted. In addition, there occurs a simultaneous sprouting of dormant rhizomes, a factor which is particularly important concerning the various perennial weeds, such as couchgrass, Johnson grass and cyperus, for these can then be easily destroyed or suppressed by herbicides. The germination capacity of seeds, such as, e.g. seed potatoes and legumes, is promoted with low concentrations, and inhibited with higher concentrations. Both the one effect and the other can be commercially important. A regulation of the blossoming time and of the number of blossoms is possible in the case of many ornamental and cultivated plants. This effect is a particularly important factor in the growing of pineapples. If all the trees or shrubs blossom at the same time, then the crops can be gathered within a comparatively short space of time. With regard to cucurbitaceae, there occurs a displacement of the blossom sex differentiation in favour of pistillate flowers.

Tests have shown that in the case of fruit trees there occurs a thinning of blossom and fruit. Furthermore, fruit ripening and fruit colouration are accelerated and improved, e.g. with oranges, melons, apricots, peaches, tomatoes, bananas, bilberries, figs, coffee, pepper, tabacco and pineapples. As a result of the development of abscission layers, the abscission of fruit and leaves is rendered appreciably more easy. This factor has great commercial significance with regard to mechanical harvesting, e.g. of citrus fruits, such as oranges, grapefruits and olives; or stone fruit such as cherries, damsons, peaches, plums and apricots; or pomaceous fruit such as apples and pears; or soft fruit such as currants, rasberries and bilberries; or nuts such as walnuts and pecan nuts; or bus-tropical fruits such as coffee, figs and pepper, or cotton. With high concentrations, the defoliation of ornamental plants, such as chrysanthemums, rhododendrons, carnations and roses, is also obtained.

The extent and the nature of the action are dependent on the most diverse factors; they are dependent particularly on the time of application with regard to the stage of development of the plant, and on the application concentration. These factors vary, however, depending on the type of plant and on the effect desired. Thus, for example, lawns are treated during the entire growth period; ornamental plants, of which, e.g. the intensity and number of the blossoms are to be increased, before development of the blossom setting; plants of which the fruit is to be sold, or in some other way utilised, immediately after blossoming, or at an appropriate interval of time before the gathering of the crop. Application of the active substances is effected by the use of solid or liquid agents, these being applied to parts of plants above the soil, to the surface of the soil, as well as into the soil itself. The preferred method is the application to the parts of plants above the soil, for which purpose solutions or aqueous suspensions are most suitable. In addition to solutions and dispersions for the treatment of the growth substrate (soil), dusts, granulates and scattering agents are also suitable.

The essential promotion of the abscission of citrus fruits and bean leaves with the use of agents according to the invention was demonstrated by the following tests.

The active substances are sprayed, in the form of solutions in concentrations of 0.2% and 0.4%, respectively, onto branches, well hung with fruit, of various orange trees. The tests are evaluated after 14 days according to the method developed by W. C. Wilson and C. H. Hendershott [Proc. Am. Soc. Hort. Sc 90, 123 – 129 (1967)]. The test consists in the measuring of the force in kilograms required to effect the abscission of the fruit.

In the case of bean-leaf abscission tests, segments of bean leaves of the type "Tempo" are immersed in a solution of 0.002% of active substance; for each active substance, 4–8 segments are left for 6 days in the active substance solution under controlled conditions. On specific days after commencement of the treatment, the number of resulting abscissions (contraction or necking of the stalk in the abscission zone on the leaf-side) is assessed.

Tests with agents containing the following active substances produced excellent results in both tests.

bis-($\beta$-bromoethyl)-divinyl-silane,
tris-($\beta$-bromoethyl)-vinyl-silane,
tetrakis-($\beta$-bromoethyl-silane,
2-bromoethyl- (dimethyl-ethoxy)-silane,
2-chloroethyl-(dimethyl-octyloxy)-silane, 2-bromoethyl-(dimethyl-hexyloxy)-silane,
2-chloroethyl-(dimethyl-benzoxy)-silane,
2-bromoethyl-(dimethyl-benzoxy)-silane,
2-chloroethyl-(dimethyl-propynyl-(2')-oxy)-silane,
2-chloroethyl-(dimethyl-butenyl-(2')-oxy)-silane, 2-chloroethyl-(dimethyl-4'-methoxybenzoxy)-silane,
2-chloroethyl-(dimethyl-acetoxy)-silane,
2-chloroethyl-(dimethyl-4'-chlorobenzoxy)-silane,
2-chloroethyl-(dimethyl-2-chloroethoxy)-silane,
2-chloroethyl-(dimethyl-hexynyl-(3')-oxy)-silane,
2-chloroethyl-(dimethyl-benzylthio)-silane,
2-chloroethyl-(dimethyl-octylthio)-silane,
2-chloroethyl-(dimethyl-benzylamino)-silane,
2-chloroethyl-(dimethyl-octadecylamino)-silane.

Agents according to the invention are produced in a manner known per se by the intimate mixing and grinding of active substances of the general formula I with suitable carriers, optionally with the addition of dispersing agents or solvents which are inert to the active substances.

Water-dispersible concentrates of active substance, i.e. wettable powders, pastes and emulsion concentrates, are active substances concentrates which can be diluted with water to obtain any desired concentration. They consist of active substance, carrier, optionally additives which stabilise the active substance, surface-active substances, and anti-foam agents and, optionally, solvents. The concentration of active substance in these agents is 0.5 –80%.

The wettable powders and pastes are obtained by the mixing and grinding of the active substances with dispersing agents and pulverulent carriers, in suitable devices, until homogeneity is attained. Suitable carriers are, e.g. the following: kaolin, talcum, bole, loess, chalk, limestone, ground limestone, Attaclay, dolomite, diatomaceous earth, precipitated silicic acid, alkaline-earth metal silicates, sodium and potassium aluminum silicates (feldspar and mica), calcium and magnesium sulphates, magnesium oxide, ground synthetic materials, fertilisers such as ammonium sulphate, ammonium phosphate, ammonium nitrate, urea, ground vegetable products such as bran, bark dust, sawdust, ground nutshells, cellulose powder, residues of plant extractions, active charcoal, etc., alone or in admixture with each other.

Suitable dispersing agents are, e.g. the following: condensation products of sulphonated naphthalene and sulphonated naphthalene derivatives with formaldehyde, condensation products of naphthalene or of naphthalene-sulphonic acids with phenol and formaldehyde, as well as alkali, ammonium and alkaline-earth metal salts of ligninsulphonic acid, also alkylarylsulphonates, alkali metal salts and alkaline-earth metal salts of dibutylnaphthalenesulphonic acid, fatty alcohol sulphates such as salts of sulphated hexadecanols, heptadecanols, octadecanols, and salts of sulphated fatty alcohol glycol ether, the sodium salt of oleyl methyl tauride, dialkyldilaurylammonium chloride and fatty acid alkali metal and akaline-earth metal salts.

Suitable anti-foam agents are for example silicones.

To these mixtures may also be added additives stabilising the active substance, and/or non-ionic, anion-active and cation-active substances, which, for example, improve the adhesiveness of the active substances on plants and on parts of plants (adhesives and agglutinants), and/or ensure a better wettability (wetting agents). Suitable adhesives are, for example, the following: olein/lime mixture, cellulose derivatives (methyl cellulose, carboxymethyl cellulose), hydroxyethylene glycol ethers of mono- and dialkylphenols having 5 –15 ethylene oxide radicals per molecule and 8 –9 carbon atoms in the alkyl radical, ligninsulphonic acid, alkali metal and alkaline-earth metal salts thereof, polyethylene glycol ethers (carbowaxes), fatty alcohol polyglycol ethers having 5 –20 ethylene oxide radicals per molecule and 8 to 18 carbon atoms in the fatty alcohol moiety, condensation products of ethylene oxide, propylene oxide, polyvinylpyrrolidones, polyvinyl alcohols, condensation products of urea/formaldehyde, as well as latex products. The active substances are so mixed, ground, sieved and strained with the above mentioned additives that the solid constituent in the case of wettable powders has a particle size not exceeding 0.02 to 0.04 mm, and in the case of pastes not exceeding 0.03 mm.

Emulsion concentrates and pastes are prepared by application of the dispersing agents such as those mentioned in the preceding paragraphs, organic solvents and water. Suitable solvents are, e.g. the following: ketones, benzene, xylenes, toluene, dimethylsulphoxide, and mineral oil fractions boiling in the range of 120° to 350°. The solvents must be practically odourless, non-phytotoxic, and inert to the active substances.

Furthermore, the agents according to the invention can be employed in the form of solutions. For this purpose, the active substance (or several active substances) of the general fomula I is (or are) dissolved in suitable organic solvents, solvent mixtures, or water. The following can be used as organic solvents: aliphatic and aromatic hydrocarbons, chlorinated derivatives thereof, alkylnaphthalenes, or mineral oils on their own or in admixture with each other. The solutions should contain the active substances in a concentration range of from 1 to 20%.

The solid preparations, such as dusts, scattering agents and granulates, contain solid carriers such as those mentioned in the foregoing, and, optionally, additives stabilising the active substance. The particle size of the carriers is for dusts advantageously up to about 0.1 mm; for scattering agents from about 0.075 mm to 0.2 mm; and for granulates 0.2 mm or coarser. The concentrations of active substance in the solid preparations are from 0.5 to 80%.

All the mentioned active substance concentrates may also contain agents stabilising against the effects of light, and antioxidants.

In the following are described several types of preparations containing active substances usable according to the invention. Where not otherwise stated, the term 'parts' denotes parts by weight.

Granulate

The following substances are used for the preparation of a 5% granulate:

5 parts of 2-chloroethyl-(dimethyl-2'-chloroethoxy)-silane,
0.25 parts of epichlorohydrin,
0.25 parts of cetyl polyglycol ether,
3.50 parts of polyethylene glycol ("carbowax"),
91 parts of kaolin (particle size 0.2 –0.8 mm).

The active substance is mixed with epichlorohydrin and the mixture dissolved in 6 parts of acetone; to the solution are then added polyethylene glycol and cetyl polyglycol ether. The thus obtained solution is sprayed on to kaolin, and the acetone subsequently evaporated in vacuo.

Wettable powder

The following constituents are used for the preparation of (a) a 40%, (b) a 50%, (c) a 25%, and (d) a 10% wettable powder:

a.
40 parts of 2-chloroethyl-(dimethyl-octyloxy)-silane,
5 parts of sodium lignin sulphonate,
1 part of sodium dibutyl-naphthalene sulphate,
54 parts of silicic acid;
b.
50 parts of 2-chloroethyl-(dimethyl-dodecyloxy)-silane,
5 parts of alkylaryl sulphonate ("Tinovertin B"),
10 parts of calcium lignin sulphonate,
1 part of Champagne chalk/hydroxyethyl cellulose mixture (1 : 1),
20 parts of silicic acid,
14 parts of kaolin;
c.
25 parts of 2-chloroethyl- (dimethyl-4'-methoxy-benzoxy)-silane,
5 parts of the sodium salt of oleylmethyl tauride,
2.5 parts of naphthalenesulphonic acid/formaldehyde condensate,
0.5 parts of carboxymethyl cellulose,
5 parts of neutral potassium aluminium silicate,
62 parts of kaoline;
d.
10 parts of 2-chloroethyl-(dimethyl-4'-chlorobenzoxy)-silane,
3 parts of a mixture of the sodium salts of saturated fatty alcohol sulphates,
5 parts of naphthalenesulphonic acid/formaldehyde condensate,
82 parts of kaolin.

The active substances are intimately mixed, in suitable mixers, with the additives; the mixture is subsequently ground in suitable mills and rollers. Wettable powders are thus obtained which can be diluted with water to give suspensions of any desired concentrations. Such suspensions are employed, e.g. for the removal of undesired side shoots, for the tillering of lawns, and for the rooting of seedlings and cuttings, etc.

Equally good wettable powders can be obtained if the active substance under (a) is replaced by 40 parts of tris-(2-bromoethyl)-vinyl-silane; or if the active substance under (b) is replaced by 50 parts of bis(2-bromoethyl)-divinyl-silane; or if the active substance under (c) is replaced by 25 parts of bis (2-bromoethyl)-methyl-vinyl-silane; or, finally, if the active substance under (d) is replaced by 10 parts of bis(2 -bromoethyl)-dimethyl-silane.

Emulsion concentrate

The following constituents are mixed together to produce 25% emulsion concentrates:
a.
25 parts of 2-chloroethyl- (dimethyl-benzoxy)-silane,
5 parts of a mixture of nonylphenolpolyoxyethylene and calcium-dodecylbenzene sulphonate,
70 parts of xylene;
b.
25 parts of 2-chloroethyl-(dimethyl-ethoxy)-silane,
10 parts of a mixture of nonylphenolpolyoxyethylene and calcium-dodecylbenzene sulphonate,
65 parts of cyclohexanone.

This concentrate can be diluted with water to obtain emulsions of any desired concentration. Such emulsions are suitable for the thinning out of blossom and fruit, for the accelerated ripening of fruits, and for the promotion of fruit and leaf abscission.

Equally good emulsions concentrates are obtained if the active substance under (a) is replaced by 25 parts of tetrakis (2-bromoethyl)-silane; or if the active substance under (b) is replaced by 25 parts of 2-bromoethyl-trivinyl-silane.

All β-halogenoethyl-silanes embraced by formula I are new compounds. The new β-halogenoethyl-dimethylsilanes of formula I wherein B and C represent the methyl group are produced according to the present invention by the reaction of a β-halogenoethyl-dimethylchloro)-silane of formula II

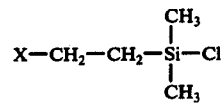 (II)

with one equivalent of one of the mercaptans, amines or alcohols of formulae III, IV and V:

The β-halogenoethyl-dimethyl-silanes of formula I (B═C═CH₃) wherein A represents the group —OR₄ can also be produced according to the present invention by the reaction of a β-halogenoethyl-dimethyl-chlorosilane of formula II:

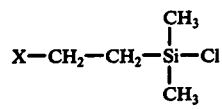 (II)

with one equivalent of an acid of the formula:

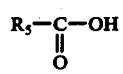

or of a carboxylic acid anhydride of the formula:

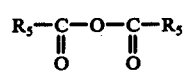

to give a compound of the formula:

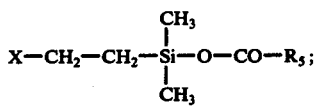

and, optionally, the exchange of the radical:

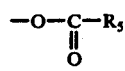

for the radical of an alcohol of formula V:

 (V)

The symbols R₁ to R₅ and X have the earlier defined meanings.

The process is preferably carried out in the presence of solvents and/or diluents which are inert to the reactants. Aprotic solvents are particularly suitable, such as, e.g. aliphatic and aromatic hydrocarbons, e.g. hexane, cyclohexane, benzene, toluene, xylene, halogenated hydrocarbons such as chlorinated ethylene, carbon tetrachloride, chloroform, chlorobenzene, also ethers and ethereal compounds such as diethyl ether, tetrahydrofuran, etc..

A complete reaction is obtained moreover where the alcohols, mercaptans or amines employed as reactants are used in excess to serve as solvents or diluents.

Furthermore, the addition of an acid-binding agent to the reaction mixture may be necessary in some cases. Suitable acid-binding agents for this purpose are, in particular, tertiary amines such as trialkylamines, e.g. triethylamine, pyridine and pyridine bases, dialkylanilines, etc..

The reaction temperatures are in the range of 0 to 100° C; the reaction duration can vary from a few minutes to several days, and depends to a great extent on the reactivity of the mercaptans, amines or alcohols employed.

The two starting materials of formula II wherein X represents chlorine or bromine are new compounds not hitherto described. β-Chloroethyl-(dimethyl-chloro)-silane is produced by methods known per se by reaction of ethyl-(dimethylchloro)-silane with chlorine, corresponding to the process described by A.D. Petrov (Doklady Akad. Nauk S.S.S.R. 100, 1107 (1955) for the production of β-chloroethyl(diethyl-chloro)-silane; or by HCl-addition to vinyl(dimethyl-chloro)-silane analogously to a mode of reaction described by G.H. Wagner et al., (Ind. Eng. Chem., 45, 367 (1953).

There is obtained in a similar manner β-bromoethyl(-dimethyl-chloro)-silane by a method known per se (cp. K.W. Michael, J.Org. Chem., 34, 2832 (1969) by reaction of ethyl-(dimethyl-chloro)-silane with bromine, or by addition of HBr to vinyl-(dimethyl-chloro)-silane (cp. A.I. Bourne, J. Chem. Soc., Sect. C, 1970, 1740).

The catalysts for the addition of HCl to vinyl(-dimethyl-chloro)-silane can be zinc chloride and other Lewis acids.

The addition of HBr to vinyl-(dimethyl-chloro)-silane is catalytically promoted by UV-light, peroxides and radical initiators.

The new β-halogenoethyl-silanes wherein all the symbols A, B and C are hydrocarbon radicals can be produced by methods known per se; for example, by reaction of corresponding ethyl-silanes with chlorine or bromine according to the process described by A.D. Petrov et al., [Doklady Akad.Nauk. S.S.S.R. 100, (1955)]; or by the process described by K.W. Michael, [J.Org. Chem. 34, 2832 (1969)] for the production of β-chloroethyldiethyl-chlorosilane or β-bromoethyl-dimethyl-chloro-silane. Preferably, however, these new β-halogenoethyl-silanes are produced by addition of HBr or HCl to vinyl-silanes, that is, to β-bromoethyl-silanes of formula Ib

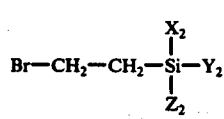
(Ib)

wherein
$Y_2$ represents —CH=CH$_2$ or —CH$_2$—CH$_2$—Br, and
$X_2$ and $Z_2$ each independently represent —CH$_3$, —CH=CH$_2$ or —CH$_2$—CH$_2$—Br, the addition being effected by reaction of vinylsilane of formula IIb

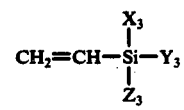
(IIb)

wherein
$Y_3$ represents —CH=CH$_2$, and
$X_3$ and $Z_3$ each independently represent —CH$_3$ or —CH=CH$_2$, in a molar ratio of at least 1:1 with hydrogen bromide; and to β-chloroethyl-silanes of formula Ic

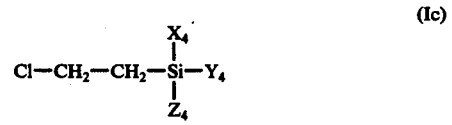
(Ic)

wherein
$Y_4$ represents —CH=CH$_2$ or —CH$_2$—CH$_2$—Cl, and
$X_4$ and $Z_4$ each independently represent —CH$_3$, —CH=CH$_2$ or —CH$_2$—CH$_2$—Cl, the addition being effected by reaction of a vinylsilane of formula IIb in a molar ratio of at least 1:1 with hydrogen chloride.

The reaction of a vinyl-silane of formula IIb with hydrogen bromide is advantageously performed by irradiation with UV-light and/or in the presence of a catalyst, such as organic peroxides or radical initiators. Suitable catalysts are, for example: dibenzoyl peroxide, diacetyl peroxide, di-tert-butyl peroxide, cumene hydroperoxide, dialkoxyazo compounds and azoisobutyronitrile.

The reaction temperatures can vary, depending on the nature of the final product desired, within wide limits; they are however advantageously between −10° C and +150° C, particularly between −10° C and +35° C. Since the reaction is intensely exothermic, it is generally performed with initial cooling of the reaction mixture. It is also possible to carry out the reaction under elevated pressure.

The reaction of a vinyl-silane of formula IIb with hydrogen chloride is advantageously performed in the presence of a Lewis acid, and optionally under elevated pressure.

The Lewis acids employed can be the compounds known from the literature: for example, aluminium chloride, aluminium bromide, iron(III)chloride, antimony pentachloride, antimony pentafluoride, tin tetrachloride, zinc chloride and boron trifluoride. The reaction is preferably performed in the presence of aluminium chloride.

In general, it is advisable to carry out the reaction at a pressure of at least 5 bars, and at a temperature of between 0° C and 60° C. It is also possible in certain cases, however, to operate at normal pressure; e.g., for the production of the β-chloroethyltrimethyl-silane known per se (cp. Sommer and Baugham, J.Am.Chem. Soc. 83, 3346 (1961).

Polyhalogenoethyl-silanes wherein the various halogens are not identical can be obtained, for example, by reaction of vinyl-silanes of formula IIb with a mixture of hydrogen chloride and hydrogen bromide, preferably with UV-light irradiation; or by reaction of β- chloroethyl-silanes of formula Ic wherein at least one of the symbols $X_4$, $Y_4$ and $Z_4$ represents $-CH=CH_2$ with hydrogen bromide in the above described manner.

The vinyl-silanes of formula IIb and the hydrogen bromide or hydrogen chloride are used, as defined, in a molar ratio of at least 1:1; preferably, however, the hydrogen bromide or hydrogen chloride is used in a ca. 5 – 60% excess above the stoichiometrically required amount.

The vinyl-silanes of formula IIb used as starting products are known; they can be produced, for example, by the action of Grignard compounds on corresponding chlorosilanes.

The following examples serve to further illustrate the process according to the invention. In the attached table there are listed further β-halogenoethyl-silanes of formula I produced by the methods described in the examples.

The temperatures are expressed in degrees Centigrade.

EXAMPLE 1

(Production of a starting material)

A 300 ml steel autoclave fitted with magnetic stirrer, thermocouple element and cooling device is charged with 60 g (0.5 mole) of vinyl-dimethyl-chlorosilane and 0.3 g of anhydrous zinc chloride. The apparatus is flushed twice with nitrogen, and hydrogen chloride then injected portionwise, with stirring, until an internal pressure of 34 bars is obtained. The temperature is raised to 40° and maintained by repeated cooling at 40° – 50° for 1 hour, during which time the consumed amount of hydrogen chloride is continuously replenished to maintain a constant pressure of 34 bars.

After cooling, the reaction product is distilled over at room temperature and 0.1 Torr, to effect the removal of the $ZnCl_2$-catalyst, into a cooling trap cooled to $-70°$; and subsequently fractionated at 60 Torr through a 10 cm Vigreux-column to obtain 7.1 g of 2-chloroethyl(-dimethyl-chloro)-silane; B.P.: 70° – 72°/60 Torr.

EXAMPLE 2

(Production of a starting material)

An amount of 725 g of vinyl-dimethyl-chlorosilane is cooled to $-5°$ to $0°$; hydrogen bromide is then fed in at this temperature, with UV-irradiation, for 45 to 60 minutes. After completion of the HBr-absorption, the unreacted hydrogen bromide is expelled with nitrogen, and the solution fractionated through a 20 cm Vigreux-column.

There is obtained 1080 g of 2-bromoethyl-(dimethyl-chloro)-silane; B.P.: 65° – 66°/13 Torr.

|    | Calculated: | Found: |
|----|-------------|--------|
| Si | 13.39       | 13.56  |

EXAMPLE 3

An amount of 60.4 g of 2-bromoethyl-(dimethyl-chloro)silane is dissolved in 36 g of acetic acid anhydride, and the solution allowed to stand in a closed vessel for 48 hours at room temperature. The solution is fractionated through a 10 cm Vigreux column.

There is obtained 19.6 g of 2-bromoethyl-(dimethylacetyloxy)-silane; B.P/: 43° – 44°/0.6 Torr.

|    | Calculated | Found: |
|----|------------|--------|
| Si | 12.5       | 12.4   |

EXAMPLE 4

An amount of 30.2 g of 2-bromoethyl-dimethyl-chlorosilane is dissolved in 350 ml of absolute diethyl ether; an addition is then made at $-5°$ to $-10°$ within 5 to 10 minutes of 6.9 g of ethyl alcohol and 11.9 of g. of absolute pyridine, both constituents dissolved together in 100 ml of absolute ether. Stirring is carried out for a further hour at 0°, and refluxing then performed for 18 hours.

The reaction mixture is filtered, and the filtrate concentrated in vacuo to obtain 13.1 g of 2-bromoethyl-(dimethyl-ethyloxy)-silane; B.P.: 67°–69°/14 Torr.

|    | Calculated: | Found: |
|----|-------------|--------|
| Si | 14.6        | 14.1   |

EXAMPLE 5

A mixture of 10.1 g of triethylamine and 10.7 g of benzylamine is dissolved in 150 of absolute diethyl ether; an addition is then made at $-5°$ to $-10°$ within one hour of 15.7 g of 2-chloroethyl-dimethyl-chlorosilane dissolved in 50 ml of absolute ether. The mixture is stirred for 24 hours at 0° and for 12 hours at room temperature. It is then filtered and the filtrate concentrated in vacuo.

There is obtained 16.8 g of 2-chloroethyl-(dimethyl-benzylamino)-silane.

EXAMPLE 6

An amount of 15.7 g of 2-chloroethyl-dimethyl-chlorosilane is dissolved in 200 ml of absolute diethyl ether; additions are then made at $-10°$ within 30 minutes firstly of 12.4 g of benzylmercaptan, and then of absolute pyridine dissolved in 50 ml of absolute ether. The mixture is stirred for 2 hours at 0° and for 2 hours at room temperature, and then refluxed for 18 hours. It is subsequently filtered and the filtrate concentrated in vacuo.

There is obtained 19.8 g of 2-chloroethyl-(dimethyl-benzylthio)-silane.

EXAMPLE 7

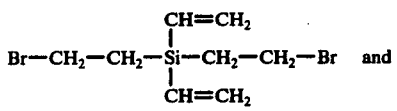

and

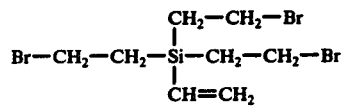

A vigorous flow of dry hydrogen bromide is fed at a temperature of $-5°$, with UV-irradiation, into 17.5 g (0.13 mole) of tetravinyl-silane. After commencement of the exothermic reaction, hydrogen bromide is further introduced with cooling ($-5°$ to 0°) until the absorption of hydrogen bromide is ca. 25 g. The reaction mixture is subsequently fractionated under 0.001 Torr through a Vigreux column to obtain 15.3 g (40% of theory) of bis-(β-bromoethyl)-divinyl-silane and 13.4 g (27% of theory) of tris-(β-bromoethyl)-vinyl-silane.

Analyses:
bis-(β-bromoethyl)-divinyl-silane; B.P.$_{0.001}$ = 78°,
Calculated: C, 32.2%; H, 4.7% Si, 9.4%; Br, 53.7%.
Found: C, 32.4%; H, 4.7%; Si, 9.8%; Br, 53.4%.
tris-(β-bromoethyl)-vinyl-silane; B.P.$_{0.01}$ = 126°.
Calculated: C, 25.3%; H, 4.0%; Si, 7.4%; Br, 63.3%.
Found: C, 25.6%; H, 3.9%; Si, 7.8%; Br, 62.4%.

EXAMPLE 8

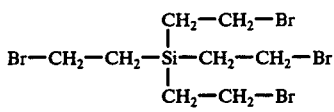

Dry hydrogen bromide is introduced, with UV-irradiation, into 20.4 g (0.15 mole) of tetravinyl-silane, with the temperature being raised from 0° to 140°. After 5-6 hours the hydrogen bromide absorption has attained a level of 93%; the reaction mixture is cooled, whereupon tetrakis-(β-bromoethyl)-silane crystallises out. After recrystallisation from carbon tetrachloride with the addition of active charcoal, there is obtained 45 g (65% of theory) of tetrakis-(β-bromoethyl)-silane, M.P. 90°-91°.

Analysis:
Calculated: C, 20.9%; H, 3.5%; Si, 6.1%; Br, 69.5%.
Found: C, 20.9%; H, 3.5%; Si, 6.0%; Br, 69.8%.

EXAMPLE 9

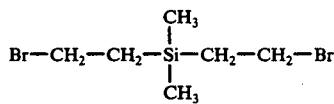

Dry hydrogen bromide is introduced, with UV-irradiation, at −5° to 0° into 17.0 g (0.151 mole) of dimethyl-divinyl-silane; the reaction occurring is intensely exothermic, and the hydrogen bromide absorption after 30 minutes is already 99%. The reaction product is fractionated at 10 Torr through a Vigreux column to obtain 31.4 g (76% of theory) of bis-(β-bromoethyl)-dimethyl-silane; B.P.$_{10}$ = 117°.

Analysis:
Calculated: C, 26.3%; H, 5.1%; Si, 10.2%; Br, 58.4%.
Found: C, 26.5%; H, 5.1%; Si, 10.4%; Br, 58.0%.

EXAMPLE 10

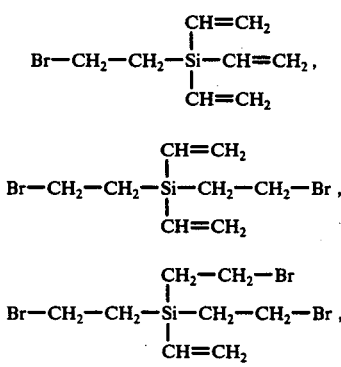

-continued

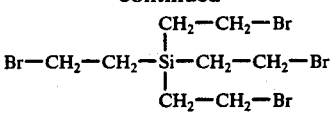

At a temperature of −5° to 0° and with exposure to UV-radiation, hydrogen bromide is fed into 54.4 g (0.4 mole) of tetravinyl-silane; the supply of hydrogen bromide is continued for ca. 90 minutes, with continuous cooling and stirring of the reaction mixture, until ca. 68 g of hydrogen bromide has been absorbed. The following β-bromoethyl-silanes are obtained after fractionating of the reaction mixture through a 10 cm Vigreux column: β-bromoethyl-trivinyl-silane, B.P.$_{0.005}$ = 38°-40° yield: 3 g (3.5% of theory);

bis-(β-bromoethyl)-divinyl-silane, B.P.$_{0.001}$ = 76°-78°, yield: 37.2 g (31.5% of theory);

tris-(β-bromoethyl)-vinyl-silane, B.P.$_{0.05}$ = 134°-137°, yield: 54.6 g (36.4% of theory).

It is possible to obtain from the distillation residue, by recrystallisation from cyclohexane or from n-hexane, a further 4 g (2.2% of theory) of tetrakis-(β-bromoethyl)-silane; M.P. 91.

A separation of the β-bromoethyl-silanes obtained is in most cases not necessary for their use in agents according to the invention.

EXAMPLE 11

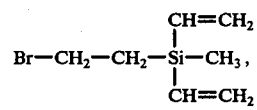

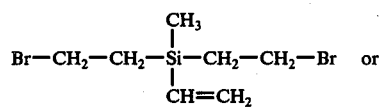

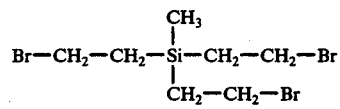

At a temperature of −10° to +35° and with exposure to UV-radiation, hydrogen bromide is fed for 4 hours into 50 g (0.4 mole) of methyl-trivinyl-silane, until an increase in weight of 79 g is recorded. The reaction mixture is fractionated through a 10 cm Vigreux-column to obtain the following β-bromoethyl-silanes:

β-bromoethyl-methyl-divinyl-silane, B.P.$_{0.01}$ = 34°-37°, yield: 3.3 g (4% of theory);

bis-(β-bromoethyl)-methyl-vinyl-silane, B.P.$_{0.01}$ = 79°-80°, yield: 49.7 g (44% of theory);

tris-(β-bromoethyl)-methyl-silane, B.P.$_{0.05}$ = 134°-135°, yield: 47.7 g (33% of theory).

If the tris-(β-bromoethyl)-methyl-silane is recrystallised from n-hexane, then a white crystalline product, M.P. 64°, is obtained.

A separation of the β-bromoethyl-silanes obtained is in most cases not necessary for their use in agents according to the invention.

EXAMPLE 12

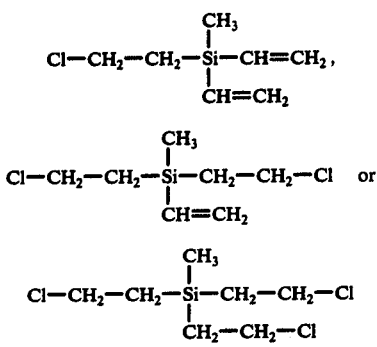

An amount of 62.1 g (0.5 mole) of methyl-trivinyl-silane is placed into a 300 ml steel autoclave fitted with magnetic stirrer, thermocouple element and cooling device and containing a nitrogen atmosphere. At a temperature of $-5°$ to $0°$, hydrogen chloride is injected portionwise until an internal pressure of 30 bars is obtained. The reaction mixture is subsequently stirred for 2½ hours at $0°$ to $20°$, while the amount of hydrogen chloride is continuously replenished to maintain a constant pressure of 30 bars. A total amount of 90 g of hydrogen chloride is injected. Fractionating of the reaction through a 10 cm Vigreux column yields the following β-chloroethyl-silanes:

β-chloroethyl-methyl-divinyl-silane, $B.P._{10}$ = 62°–65°, yield: 19 g (23.7% of theory);

bis-β-chloroethyl)-methyl-vinyl-silane, $B.P._{0.01}$ = 64°–67°, yeild: 20.7 g (21% of theory);

tris-(β-chloroethyl)-methyl-silane, $B.P._{0.001}$ = 98°–103°, yield: 4.0 g (3.5% of theory).

Table 1

Compounds of formula $$X-CH_2-CH_2-\underset{\underset{CH_3}{|}}{\overset{\overset{CH_3}{|}}{Si}}-A$$

$A = O-R_4$

| | $R_4$ | X | Physical data |
|---|---|---|---|
| 1 | Ethyl | Cl | |
| 2 | Ethyl | Br | B.P. 67 – 69°/14 Torr |
| 3 | n-Butyl | Cl | |
| 4 | Isobutyl | Cl | |
| 5 | sec.Butyl | Cl | |
| 6 | Isopropyl | Cl | |
| 7 | Hexyl | Br | B.P. 131°/0.4 Torr |
| 8 | 2-Methylbutyl | Cl | |
| 9 | 3-Methylbutyl | Cl | |
| 10 | 1,3-Dimethylbutyl | Cl | |
| 11 | Octyl | Cl | |
| 12 | 1-Methylheptyl | Cl | |
| 13 | Decyl | Br | |
| 14 | Undecyl | Cl | |
| 15 | Dodecyl | Cl | |
| 16 | Hexadecyl | Cl | |
| 17 | Octadecyl | Cl | |
| 18 | 2-Chloroethyl | Cl | |
| 19 | 6-Chlorohexyl | Cl | |
| 20 | 6-Chlorohexyl | Br | |
| 21 | 2-Methoxyethyl | Cl | |
| 22 | 2-Ethoxyethyl | Cl | |
| 23 | 2-Isopropyloxyethyl | Cl | |
| 24 | 2-Propyloxyethyl | Cl | |
| 25 | 2-Butyloxyethyl | Cl | |
| 26 | 2-Hexyloxyethyl | Br | |
| 27 | 2-(2-Ethoxyethoxy)ethyl | Cl | |
| 28 | 2-(2-Methoxyethoxy)ethyl | Cl | |
| 29 | 2-(2-Butyloxyethoxy)ethyl | Br | |
| 30 | 2-[2-(1-Undecylcarboxy)ethoxy]ethyl | Cl | |
| 31 | 2-[2-(1-Heptadecylcarboxy) ethoxy]-ethyl | Cl | |
| 32 | 2-Formamidoethyl | Cl | |
| 33 | 2-Allyloxyethyl | Cl | |
| 34 | 2-Ethylthioethyl | Cl | |
| 35 | 2-Octylthioethyl | Cl | |
| 36 | 3-Phenylpropyl | Br | |
| 37 | 2-Phenylethyl | Cl | |
| 38 | 2-Phenoxyethyl | Cl | |
| 39 | 2-Propenyl | Cl | |
| 40 | 2-Butenyl | Cl | |
| 41 | 2-Butenyl | Br | B.P. 80 – 82° /0.15 |
| 42 | 3,7-Dimethyl-2-octenyl | Cl | |
| 43 | 10-Undecenyl | Cl | |
| 44 | 9-Octadecenyl | Cl | |
| 45 | 3,7-Dimethyl-7-octenyl | Cl | |
| 46 | 3,7-Dimethyl-2,6-octadienyl | Br | $n_D^{20}$ – 1,4748 |
| 47 | 2-Propynyl | Cl | |
| 48 | 2-Propynyl | Br | |
| 49 | 1-Propyl-2-propinyl | Cl | |
| 50 | 3-Hexynyl | Cl | |
| 51 | 3-Chloro-2-butenyl | Cl | |
| 52 | 3-Phenyl-2-propenyl | Cl | |
| 53 | 3-Phenyl-2-propenyl | Br | $n_D^{20}$ = 1.5490 |
| 54 | 2-(1-Methylethenyl)ethyl | Cl | |
| 55 | 2-Cyanoethyl | Cl | |
| 56 | Ethoxycarbonylmethyl | Cl | |
| 57 | 1-Ethoxycarbonyl(1-methyl)- | Br | |

Table 1-continued

Compounds of formula $$X-CH_2-CH_2-\underset{\underset{CH_3}{|}}{\overset{\overset{CH_3}{|}}{Si}}-A$$

$A = O-R_4$

| | $R_4$ | X | Physical data |
|---|---|---|---|
| | methyl | | |
| 58 | Butoxycarbonylmethyl | Cl | |
| 59 | Cyclohexyl | Cl | |
| 60 | Cyclohexylmethyl | Cl | |
| 61 | 3-Cyclohexylpropyl | Br | |
| 62 | 3,4-Dimethylcyclohexyl | Cl | |
| 63 | 3,5-Dimethylcyclohexyl | Cl | |
| 64 | 4-tert.Butylcyclohexyl | Br | |
| 65 | (-)-Borneyl | Cl | |
| 66 | 6,6-Dimethylbicyclo(3.1.1.)hept-2-ene-2-ethyl | Cl | |
| 67 | Benzyl | Cl | B.P. 90 – 95° /0.3 |
| 68 | Benzyl | Br | B.P. 85 – 87° /0.08 |
| 69 | 4-Chlorobenzyl | Cl | |
| 70 | 4-Chlorobenzyl | Br | |
| 71 | 4-Methoxybenzyl | Cl | |
| 72 | 2,4-Dichlorbenzyl | Cl | |
| 73 | 4-Methylbenzyl | Cl | |
| 74 | Phenyl | Cl | |
| 75 | 4-Chlorophenyl | Cl | |
| 76 | 3-Chlorophenyl | Cl | |
| 77 | 3,4-Dichlorophenyl | Cl | |
| 78 | 3,5-Dichlorophenyl | Cl | |
| 79 | 4-Bromophenyl | Cl | |
| 80 | 4-Methoxyphenyl | Cl | |
| 81 | 4-Methoxyphenyl | Br | $n_D^{20} = 1.4708$ |
| 82 | 3-Methoxyphenyl | Cl | |
| 83 | 4-Butyloxyphenyl | Cl | |
| 84 | 4-tert.Butylphenyl | Cl | |
| 85 | 3-Methylphenyl | Cl | |
| 86 | 3-Methylphenyl | Br | |
| 87 | 3,4-Dimethylphenyl | Cl | |
| 88 | 3-Formylphenyl | Cl | |
| 89 | 4-Cyanophenyl | Cl | |
| 90 | 4-Ethoxycarbonylphenyl | Cl | |
| 91 | 3-Ethoxycarbonylphenyl | Cl | |
| 92 | ⟨tetrahydropyran-2-yl⟩CH₂— | Cl | |
| 93 | ⟨furan-2-yl⟩CH₂— | Cl | |
| 94 | ⟨thiophen-2-yl⟩CH₂— | Cl | |
| 95 | ⟨tetrahydrofuran-2-yl⟩CH₂— | Cl | |
| 96 | ⟨5-methyl-1,3-dioxan-5-yl⟩CH₂— | Cl | |
| 97 | ⟨2,2-dimethyl-1,3-dioxolan-4-yl⟩CH₂— | Cl | |
| 98 | ⟨pyridin-4-yl⟩CH₂CH₂— | Cl | |
| 99 | (CH₃)₂N⁺(H)(Cl⁻)—CH₂CH₂— | Cl | |

Table 2

$A = O-R_4$; $R_4 = -CO-R_5$

| | $R_5$ | X | Physical data |
|---|---|---|---|
| 100 | Methyl | Cl | |
| 101 | Methyl | Br | B.P. 43 – 44°/0.6 Torr |
| 102 | Ethyl | Cl | |
| 103 | Ethyl | Br | |
| 104 | Isopropyl | Cl | |
| 105 | 1-Butylpropyl | Cl | |
| 106 | Pentyl | Cl | |
| 107 | Octyl | Cl | |
| 108 | Heptyl | Cl | |
| 109 | Undecyl | Cl | |
| 110 | Pentadecyl | Cl | |
| 111 | Heptadecyl | Cl | |
| 112 | 2-Propenyl | Cl | |
| 113 | 2-Propenyl | Br | |
| 114 | 1-Propenyl | Cl | |
| 115 | 9-Decenyl | Cl | |
| 116 | 1,3-Pentadienyl | Cl | |
| 117 | 8,11-Heptadecadienyl | Cl | |
| 118 | 2-Chloroethyl | Cl | |
| 119 | 2-Bromoethyl | Cl | |
| 120 | 1-Bromopentyl | Cl | |
| 121 | 10-Bromodecyl | Cl | |
| 122 | 10-Bromodecyl | Br | |
| 123 | cis-2-Chloroethenyl | Cl | |
| 124 | cis-2-Chloroethenyl | Br | |
| 125 | Phenylmethyl | Cl | |
| 126 | 2-Phenylethyl | Cl | |
| 127 | 4-Chlorophenylmethyl | Cl | |
| 128 | 3-Methylphenyl | Cl | |
| 129 | 2-(4'-Methoxyphenyl)ethyl | Cl | |
| 130 | 4-Ethoxycarbonylbutyl | Cl | |
| 131 | 3-Oxobutyl | Cl | |
| 132 | 3-Oxobutyl | Br | |
| 133 | 5-Phenyl-5-oxopentyl | Cl | |
| 134 | 2-Ethoxyethyl | Cl | |
| 135 | 3-Phenoxypropyl | Cl | |
| 136 | 2,4-Dichlorophenoxymethyl | Cl | |
| 137 | 2,4-Dichlorophenoxymethyl | Br | |
| 138 | 2-(4'-Chlorophenyl)-1-ethenyl | Cl | |
| 139 | 2-Phenyl-1-ethenyl | Br | |
| 140 | 2-(3'4'-Dichlorophenyl)-1-ethenyl | Cl | |
| 141 | 2-(4'-Methoxyphenyl)-1-ethenyl | Cl | |
| 142 | Cyclohexyl | Cl | |
| 143 | Cyclohexylmethyl | Cl | |
| 144 | Cyclohexylmethyl | Br | |
| 145 | Cyclopropyl | Cl | |
| 146 | Cyclopropyl | Br | |
| 147 | 3-Cyclohexenyl | Cl | |
| 148 | 3-Cyclohexenyl | Br | |
| 149 | 2-Cyclopentene-1-methyl | Cl | |
| 150 | 2-Cyclopentene-1-methyl | Br | |
| 151 | Phenyl | Cl | |
| 152 | 4-Chlorophenyl | Cl | |
| 153 | 4-Methoxyphenyl | Cl | |
| 154 | 4-Methylphenyl | Cl | |
| 155 | 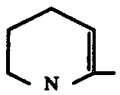 | Cl | |
| 156 | | Cl | |
| 157 | | Br | |
| 158 | | Cl | |

Table 3

$A = -N\begin{smallmatrix}R_2\\R_3\end{smallmatrix}$

| | $R_2$ | $R_3$ | X | Physical data |
|---|---|---|---|---|
| 159 | Ethyl | Ethyl | Cl | |
| 160 | H | Butyl | Cl | |
| 161 | H | Butyl | Br | |
| 162 | H | Octyl | Cl | |

Table 3-continued $A = -N\begin{smallmatrix}R_2\\R_3\end{smallmatrix}$

| | $R_2$ | $R_3$ | X | Physical data |
|---|---|---|---|---|
| 163 | H | Dodecyl | Cl | |
| 164 | H | Dodecyl | Br | |
| 165 | H | Octadecyl | Cl | |
| 166 | H | 2-Propenyl | Cl | |
| 167 | H | 9-Octadecenyl | Br | 1.4664 |
| 168 | H | 2-Propynyl | Cl | |
| 169 | H | 1,2,2,-Trimethylpropyl | Cl | |
| 170 | H | 1-Methylhexyl | Cl | |
| 171 | H | Pentyl | Cl | |
| 172 | H | Decyl | Cl | |
| 173 | H | 2-ethylhexyl | Cl | |
| 174 | H | Hexadecyl | Cl | |
| 175 | H | Cyclohexyl | Cl | |
| 176 | H | Cyclohexylmethyl | Cl | |
| 177 | H | 2-Methoxyethyl | Cl | |
| 178 | H | 3-Isopropyloxypropyl | Cl | |
| 179 | H | 2,2-Diphenylethyl | Cl | |
| 180 | H | Benzyl | Cl | |
| 181 | H | Benzyl | Br | |
| 182 | H | 4-Chlorobenzyl | Cl | |
| 183 | H | 3-Chlorobenzyl | Cl | |
| 184 | H | 3,4-Dichlorobenzyl | Cl | |
| 185 | H | 4-Methoxybenzyl | Cl | |
| 186 | H | Phenyl | Cl | |
| 187 | H | 4-Bromophenyl | Cl | |
| 188 | H | 4-Methoxyphenyl | Cl | |
| 189 | H | 4-Methylthiophenyl | Br | 1.5826 |
| 190 | H | 3-Methylphenyl | Cl | |
| 191 | Methyl | Benzyl | Cl | |
| 192 | H | | Cl | |
| 193 | H | 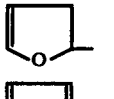 | Cl | |
| 194 | H | | Cl | |
| 195 | | 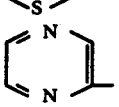 | Br | |

Table 4

$A = S-R_1$

| | $R_1$ | X | Physical data |
|---|---|---|---|
| 196 | Ethyl | Cl | |
| 197 | Butyl | Cl | |
| 198 | Octyl | Cl | |
| 199 | Octyl | Br | |
| 200 | Dodecyl | Cl | |
| 201 | Octadecyl | Cl | |
| 202 | Methoxycarbonylethyl | Cl | |
| 203 | 3-Phenylpropyl | Cl | |
| 204 | Cyclohexyl | Cl | |
| 205 | 2-Propenyl | Cl | |
| 206 | Phenyl | Cl | |
| 207 | Phenyl | Br | |
| 208 | 4-Bromophenyl | Cl | |
| 209 | 4-Chlorophenyl | Cl | |
| 210 | 4-tert.Butylphenyl | Cl | |
| 211 | 4-Bromo-3-methylphenyl | Cl | |
| 212 | 4-Methoxyphenyl | Cl | |
| 213 | 4-Methoxyphenyl | Br | |
| 214 | 3-Methylphenyl | Cl | |
| 215 | Benzyl | Cl | |
| 216 | Benzyl | Br | |
| 217 | 4-Chlorobenzyl | Cl | |
| 218 | 4-Chlorobenzyl | Br | |
| 219 | 3,4-Dimethylphenyl | Cl | |

We claim:

1. A beta-halogenoethyl silane corresponding to the formula

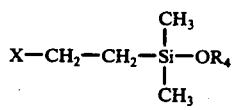

in which X is chlorine or bromine; and $R_4$ is $C_1$–$C_{18}$ alkyl; $C_1$–$C_{18}$ alkyl substituted by halogen, phenyl, or $C_3$–$C_{12}$ cycloalkyl; $C_3$–$C_{18}$ alkenyl; $C_3$–$C_{18}$ halogenoalkenyl; $C_3$–$C_8$ alkynyl; $C_3$–$C_{12}$ cycloakyl; $C_3$–$C_{12}$ cycloalkenyl; phenyl; phenyl mono- or poly- substituted by $C_1$–$C_8$ alkyl, or $C_1$–$C_6$ halogenoalkyl; benzyl; or benzyl mono- or polysubstituted by $C_1$–$C_8$ alkyl or halogen.

2. The silane of claim 1, wherein $R_4$ is $C_1$–$C_{18}$ alkyl; $C_1$–$C_{18}$ alkyl substituted by halogen; benzyl; or benzyl substituted by $C_1$–$C_8$ alkyl or halogen.

3. The silane of claim 2 which is beta-bromoethyl-dimethyl-n-hexyloxy silane.

4. The silane of claim 2 which is beta-bromoethyl-dimethyl-benzyloxy-silane.

5. The silane of claim 2 which is beta-bromoethyl-dimethyl-ethyloxy-silane.

6. The silane of claim 2 which is beta-chloroethyl-dimethyl-benzyloxy silane.

* * * * *